(12) United States Patent
Kumar et al.

(10) Patent No.: US 9,393,205 B2
(45) Date of Patent: Jul. 19, 2016

(54) GASTRORETENTIVE TABLETS

(71) Applicant: RANBAXY LABORATORIES LIMITED, New Delhi, Delhi (IN)

(72) Inventors: Varinder Kumar, Mohali (IN); Shavej Ahmad, Lucknow (IN); Romi Barat Singh, Varanasi (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 0 days.

(21) Appl. No.: 14/374,568

(22) PCT Filed: Jan. 29, 2013

(86) PCT No.: PCT/IB2013/050764
§ 371 (c)(1),
(2) Date: Jul. 25, 2014

(87) PCT Pub. No.: WO2013/114283
PCT Pub. Date: Aug. 8, 2013

(65) Prior Publication Data
US 2015/0025146 A1    Jan. 22, 2015

(30) Foreign Application Priority Data
Jan. 30, 2012  (IN) .............................. 250/DEL/2012
Jan. 30, 2012  (IN) .............................. 252/DEL/2012

(51) Int. Cl.
| | | |
|---|---|---|
| *A61K 31/197* | (2006.01) | |
| *A61K 9/20* | (2006.01) | |
| *A61K 9/00* | (2006.01) | |

(52) U.S. Cl.
CPC ............. *A61K 9/2054* (2013.01); *A61K 9/0065* (2013.01); *A61K 9/205* (2013.01); *A61K 9/2009* (2013.01); *A61K 9/2013* (2013.01); *A61K 9/2018* (2013.01); *A61K 9/2027* (2013.01); *A61K 9/2031* (2013.01); *A61K 9/2095* (2013.01); *A61K 31/197* (2013.01)

(58) Field of Classification Search
CPC ........................... A61K 31/197; A61K 9/2054
USPC ............................................ 514/561; 424/465
See application file for complete search history.

(56) References Cited

U.S. PATENT DOCUMENTS

| | | | |
|---|---|---|---|
| 5,563,175 A | 10/1996 | Silverman et al. | 514/561 |
| 6,001,876 A | 12/1999 | Singh | 514/561 |
| 6,117,906 A | 9/2000 | Silverman et al. | 514/561 |
| 6,197,819 B1 | 3/2001 | Silverman et al. | 514/561 |
| 2007/0269511 A1 | 11/2007 | Bockbrader et al. | 424/468 |
| 2010/0255067 A1 | 10/2010 | Sammohi et al. | 424/443 |
| 2011/0135723 A1 | 6/2011 | Kshirsagar et al. | 424/465 |

FOREIGN PATENT DOCUMENTS

WO    WO 2011/151708    12/2011 ........... A61K 31/197

*Primary Examiner* — Raymond Henley, III

(57) ABSTRACT

The present invention relates to a gastroretentive tablet comprising pregabalin, at least one swellable polymer, and other pharmaceutically acceptable excipients. It further relates to a process for the preparation of same.

10 Claims, No Drawings

GASTRORETENTIVE TABLETS

FIELD OF THE INVENTION

The present invention relates to a gastroretentive tablet comprising pregabalin, at least one swellable polymer, and other pharmaceutically acceptable excipients. It further relates to a process for the preparation of the same.

BACKGROUND OF THE INVENTION

Pregabalin, or (S)-3-(aminomethyl)-5-methylhexanoic acid, binds to the calcium channel alpha-2-delta ($\alpha 2\delta$) subunit and is related to endogenous inhibitory neurotransmitter gamma-amino butyric acid (GABA), which is involved in brain neuronal activity. In the United States, pregabalin has been approved for the management of neuropathic pain associated with diabetic peripheral neuropathy, management of post herpetic neuralgia, management of fibromyalgia, and as an adjunctive therapy for adult patients with partial onset seizures.

Pregabalin is disclosed in U.S. Pat. Nos. 6,197,819 and 5,563,175, which describe its use in the treatment of seizure disorders. U.S. Pat. No. 6,117,906 discloses the use of pregabalin in treating anxiety, while U.S. Pat. No. 6,001,876 discloses its use in treating pain.

Currently, pregabalin is available as conventional immediate-release capsules marketed by CP Pharms/Pfizer under the brand name Lyrica®, Lyrica® requires two or three times a day dosing. The importance of taking drugs at regular intervals cannot be overemphasized. However, it is not easy for everyone to remember to take the correct dose at the same time each day. Multiple dosing is not only inconvenient but it also lowers patient compliance. Once daily dosing generally improves patient compliance as well as reduces the severity and frequency of side effects by reducing peak blood levels and may also increase drug efficacy by increasing minimum plasma concentration. Once daily dosing of pregabalin, however, presents numerous challenges. Conventional extended-release compositions are problematic as pregabalin does not have uniform absorption throughout the entire gastrointestinal tract. Pregabalin is absorbed well in the small intestine and the ascending colon, but is poorly absorbed beyond the hepatic flexure. This suggests that the mean absorption window for pregabalin is, on average, about six hours or less and any drug-release from a conventional extended-release dosage form beyond six hours would thus be wasted because the dosage form has travelled beyond the hepatic flexure.

U.S. Publication Application No. 2007/0269511 discloses a pregabalin formulation containing matrix forming agent and a swelling agent wherein the matrix forming agent is polyvinyl acetate and polyvinylpyrrolidone, and the swelling agent is cross-linked polyvinylpyrrolidone. U.S. Publication Application No. 2011/0135723 describes once-daily pharmaceutical compositions of pregabalin wherein the excipients include one or more water-insoluble components, or a combination of one or more water-insoluble components and one or more water-soluble components. U.S. Publication Application No. 2010/0255067 describes pharmaceutical compositions comprising pregabalin, a hydrophobic release controlling agent, and other pharmaceutically acceptable excipients. PCT Publication No. WO 2011/151708 describes a gastroretentive dosage form comprising a GABA analog, at least one swelling agent, and at least one non-swelling release retardant.

Therefore, a sustained-release gastroretentive dosage form would be an ideal dosage form for drug candidates like pregabalin. The objective of the present invention is to develop a gastroretentive tablet of pregabalin that not only extends the release of pregabalin but also retains pregabalin in the upper parts of the gastrointestinal tract for a long period of time to overcome its decreased colonic absorption.

SUMMARY OF THE INVENTION

One general aspect of the invention relates to a gastroretentive tablet comprising pregabalin, at least one swellable polymer, and other pharmaceutically acceptable excipients.

In one embodiment of the above aspect, the gastroretentive tablet may further comprise a gas generating agent.

In another embodiment, the other pharmaceutically acceptable excipients may be selected from diluents, binders, disintegrants, glidants, lubricants, and coloring agents.

In another embodiment, the swellable polymer may be selected from cellulose polymers, gums, polyethylene oxide, carbomer, superdisintegrant polymers, and combinations thereof.

In another embodiment, the gas generating agent may be selected from carbonates, bicarbonates, sufites, and mixtures thereof. The gas generating agent may additionally comprise an acid source.

In an embodiment of the above aspect, the tablet may additionally contain a matrix forming agent. The matrix forming agent may be a formulated mixture of polyvinyl acetate and polyvinylpyrrolidone.

In another general aspect, the present invention relates to a process for the preparation of a gastroretentive tablet comprising pregabalin, at least one swellable polymer, and other pharmaceutically acceptable excipients selected from diluents, binders, disintegrants, glidants, lubricants, and coloring agents, wherein the process comprises the conventional methods of dry granulation, wet granulation or direct compression.

In an embodiment of the above aspect, the process of preparation may include using a gas generating agent.

DETAILED DESCRIPTION OF THE INVENTION

"Pregabalin", as recited herein, means pregabalin or a pharmaceutically acceptable form of pregabalin, including without limitation, its free form (zwitterion) and its pharmaceutically acceptable complexes, salts, enantiomers, solvates, hydrates, and polymorphs.

One of the approaches that can be used for achieving gastric retention involves the use of swelling and expanding systems. These systems are usually monolithic tablets and are comprised of drug and one or more swellable polymers/swellable agents. These polymers/agents swell unrestrained via imbibition of gastric fluid to such an extent so that the tablet floats on gastric contents. The air entrapped by the swollen polymer confers buoyancy to the tablets. The swellable polymers that may be used in the present invention include swellable grades of cellulosic polymers such as alkyl celluloses, carboxyalkyl celluloses, hydroxyalkyl celluloses, e.g., methylcellulose, hyrdoxymethylcellulose, hydroxyethylcellulose, hydroxypropylcellulose, hydroxypropylmethylcellulose, ethyl cellulose, or mixtures thereof; polysaccharides such as starch and starch-based polymers, chitosan, gums of plant, animal, mineral or synthetic origin such as agar, alginates, carrageenan, furcellaran, guar gum, gum arabic, gum tragacanth, karaya gum, locust bean gum, pectin, dextran, gellan gum, rhamsan gum, welan gum, xanthan gum, propylene glycol alginate, hydroxypropyl guar, or mixtures thereof; acrylic acid polymer, also known as carbomer available under the tradename Carbopol®; vinyl pyrrolidone polymer such as crosslinked polyvinylpyrrolidone or crospovidone; copolymers of vinyl pyrrolidone and vinyl acetate, or mixtures thereof; polyalkylene oxides, preferably polyethylene oxide available under the trade name Polyox™, polyethylene oxide-polypropylene oxide block copolymers available under the trade names Pluronic® and Tectonics™; and superdisintegrant polymer such as cross-linked polyvinylpyrrolidone, cross-linked sodium carboxymethylcellulose, carboxymethyl starch, sodium carboxymethyl starch, potassium methacrylate-divinylbenzene copolymer, polyvinyl alcohols, starch derivatives, microcrystalline cellulose and cellulose derivatives, and alpha-, beta- and gamma-cyclodextrin and dextrin derivatives.

The swellable polymers may be used individually or in combination. In preferred embodiments, the swellable polymers include hydroxypropylmethylcellulose, hydroxyethylcellulose, gums, polyethylene oxide, xanthan gum, guar gum, sodium alginate, carbopol, crospovidone, croscarmellose sodium, or their combinations.

The term "gas generating agent", as recited herein, may include a single component that generates gas upon contact with gastric fluid, or may include a gas generating couple. Gas generating components that may be used in the present invention include carbonates such as calcium carbonate or sodium glycine carbonate; bicarbonates such as sodium bicarbonate or potassium bicarbonate; sulfites such as sodium sulfite, sodium bisulfite, or sodium metabisulfite; and the like. These salts may be used alone or in combination with an acid source as a gas generating couple. The acid source may be an edible organic acid, a salt of an edible organic acid, or mixture thereof. Examples of organic acids that may be used include citric acid, malic acid, succinic acid, tartaric acid, fumaric acid, ascorbic acid, glutamic acid, and their salts, and mixtures thereof.

The tablets may additionally comprise matrix forming agents. One of the examples of a matrix forming agent is a formulated mixture of polyvinyl acetate and polyvinylpyrrolidone available from BASF under the trade name Kollidon® SR.

The tablets may comprise other pharmaceutically acceptable excipients that are routinely used and may be selected from diluents, binders, disintegrants, glidants, lubricants, coloring agents, and mixtures thereof.

Exemplary diluents may include, but are not limited to, microcrystalline cellulose, silicified microcrystalline cellulose, microfine cellulose, lactose, starch, pregelatinized starch, calcium carbonate, calcium sulfate, sugar, mannitol, sorbitol, dextrates, dextrin, maltodextrin, dextrose, dibasic calcium phosphate dihydrate, tribasic calcium phosphate, magnesium carbonate, magnesium oxide, or combinations thereof.

Exemplary binders may include, but are not limited to, acacia, guar gum, alginic acid, carbomer, dextrin, maltodextrin, methylcellulose, ethyl cellulose, hydroxyethylcellulose, hydroxypropylcellulose, hydroxypropylmethylcellulose, carboxymethylcellulose sodium, magnesium aluminum silicate, polymethacrylates, crospovidones, povidones, copovidones, gelatin, starch, or combinations thereof.

Exemplary disintegrants include, but are not limited to, mannitol, alginic acid, carboxymethylcellulose, hydroxypropylcellulose, microcrystalline cellulose, croscarmellose sodium, crospovidone, magnesium aluminum silicate, methylcellulose, povidone, sodium alginate, sodium starch glycolate, starch, or combinations thereof.

Exemplary lubricants/glidants include, but are not limited to, magnesium stearate, zinc stearate, calcium stearate, stearic acid, colloidal silicon dioxide, glyceryl palmitostearate, vegetable oils, polyethylene glycols, polyvinyl alcohols, talc, sodium benzoate, sodium stearyl fumarate, magnesium oxide, poloxamer, sodium lauryl sulphate, polyoxyethylene monostearate, cocoa butter, hydrogenated vegetable oils, mineral oil, polysaccharides, or combinations thereof.

Exemplary coloring agents include, but are not limited to, titanium dioxide pigments, lake colors, iron oxide pigments, or combinations thereof.

The tablets prepared may further be optionally coated. Coatings may be employed for aesthetic purpose, for stabilizing the tablets, or for retarding drug-release. The coating may be carried out using conventional techniques employing conventional ingredients. For example, the tablets may be coated with one of the commercially available coating systems or any one of polymeric film coatings routinely used such as ethyl cellulose, hydroxypropylmethylcellulose, hydroxypropylcellulose, methylcellulose, carboxymethyl cellulose, hydroxyl methylcellulose, cellulose acetate, waxes such as polyethylene glycol, methacrylic acid polymers, and the like.

The tablets described herein may be prepared by conventional processes using commonly available equipment. The process may comprise involving wet granulation, dry granulation, or direct compression processes.

The gastroretentive tablets of pregabalin as described herein may take the form of several different embodiments.

In one embodiment, the gastroretentive tablet comprises pregabalin, one or more swellable polymers selected from polyethylene oxide, hydroxypropylmethylcellulose, xanthan gum, sodium alginate, and other pharmaceutically acceptable excipients.

In another embodiment, the gastroretentive tablet comprises pregabalin, one or more swellable polymers selected from hydroxypropylmethylcellulose, hydroxyethylcellulose, xanthan gum, carrageenan, crospovidone, croscarmellose sodium, and other pharmaceutically acceptable excipients.

In the above embodiments, the gastroretentive tablet may additionally comprise Kollidon® SR.

In another embodiment, the gastroretentive tablet comprises pregabalin, swelling agent(s), gas generating agent(s), citric acid, and other pharmaceutically acceptable excipients.

In another embodiment, the gastroretentive tablet comprises pregabalin, swelling agent(s), sodium bicarbonate, citric acid, and other pharmaceutically acceptable excipients.

In another embodiment, the gastroretentive tablet comprises pregabalin, swelling agent(s), sodium carbonate, citric acid, and other pharmaceutically acceptable excipients.

In another embodiment, the present invention relates to a process for the preparation of a gastroretentive tablet comprising pregabalin, at least one swellable polymer, and other pharmaceutically acceptable excipients using the conventional direct compression method comprising the steps of:
 a) Pregabalin, swellable polymer(s) and other pharmaceutically acceptable excipients are sifted through a suitable sieve and thoroughly blended for a desired time;
 b) Magnesium stearate is separately sifted through a suitable sieve;
 c) Material of step a) is blended with the material of step b) for a suitable time; and
 d) The lubricated blend of step c) is compressed into tablets using appropriate tooling.

In another embodiment, the present invention relates to a process for the preparation of a gastroretentive tablet comprising pregabalin, swelling agent(s), a gas generating agent, and other pharmaceutically acceptable excipients using the conventional direct compression method comprising the steps of:

a) Pregabalin, swelling agent(s), gas generating agent, and other pharmaceutically acceptable excipients are sifted through a suitable sieve and thoroughly blended for a desired time;
b) Magnesium stearate is separately sifted through a suitable sieve;
c) Material of step a) is blended with the material of step b) for a suitable time; and
d) The lubricated blend of step c) is compressed into tablets using appropriate tooling.

From the above, it is apparent that various modifications and combinations of the formulations detailed in the text may be made without departing from the spirit and scope of the invention. The invention as described herein may be illustrated by the following examples but is not to be construed to be limited by them.

Examples 1-4

| | Quantity (mg/tablet) | | | |
|---|---|---|---|---|
| Ingredients | Example 1 | Example 2 | Example 3 | Example 4 |
| Pregabalin | 330.00 | 330.00 | 330.00 | 330.00 |
| Polyethylene oxide | 639.00 | 300.00 | — | — |
| Hydroxypropyl-methylcellulose | 254.00 | 308.00 | — | — |
| Xanthan gum | — | — | 350.00 | 350.00 |
| Sodium alginate | — | — | — | 364.00 |
| Mannitol | — | 150.00 | — | — |
| Microcrystalline cellulose | — | — | 364.00 | — |
| Colloidal silicon dioxide | — | — | 50.00 | 50.00 |
| Magnesium stearate | 12.00 | 12.00 | 6.00 | 6.00 |
| Total weight | 1235.00 | 1100.00 | 1100.00 | 1100.00 |

Procedure:
a) Pregabalin, swellable polymer(s), and other pharmaceutically acceptable excipients are sifted through a suitable sieve and thoroughly blended for a desired time;
b) Magnesium stearate is separately sifted through a suitable sieve;
c) Material of step a) is blended with the material of step b) for a suitable time; and
d) The lubricated blend of step c) is compressed into tablets using appropriate tooling.

Examples 5-10

| | Quantity (mg/tablet) | | | | | |
|---|---|---|---|---|---|---|
| Ingredients | Example 5 | Example 6 | Example 7 | Example 8 | Example 9 | Example 10 |
| Pregabalin | 330.00 | 330.00 | 330.00 | 330.00 | 330.00 | 330.00 |
| Hydroxypropyl methylcellulose | 247.00 | 247.00 | 247.00 | 247.00 | 529.00 | 258.00 |
| Hydroxyethyl cellulose | 55.00 | 55.00 | 55.00 | 55.00 | 55.00 | — |
| Xanthan gum | — | — | 282.00 | — | — | — |
| Carrageenan | — | — | — | 282.00 | — | — |
| Crospovidone | 282.00 | — | — | — | — | — |
| Croscarmellose sodium | — | 282.00 | — | — | — | — |
| Kollidon ® SR | 309.00 | 309.00 | 309.00 | 309.00 | 309.00 | 200.00 |
| Silicon dioxide | 6.00 | 6.00 | 6.00 | 6.00 | 6.00 | 6.00 |
| Magnesium stearate | 6.00 | 6.00 | 6.00 | 6.00 | 6.00 | 6.00 |
| Total weight | 1235.00 | 1235.00 | 1235.00 | 1235.00 | 1235.00 | 800.00 |

Procedure:
a) Pregabalin, swellable polymer(s), and other pharmaceutically acceptable excipients are sifted through a suitable sieve and thoroughly blended for a desired time;
b) Magnesium stearate is separately sifted through a suitable sieve;
c) Material of step a) is blended with the material of step b) for a suitable time; and
d) The lubricated blend of step c) is compressed into tablets using appropriate tooling.

Examples 11-15

| | Quantity (mg/tablet) | | | | |
|---|---|---|---|---|---|
| Ingredients | Example 11 | Example 12 | Example 13 | Example 14 | Example 15 |
| Pregabalin | 330.00 | 330.00 | 330.00 | 330.00 | 300.00 |
| Hydroxypropylmethyl cellulose | 280.00 | — | 90.00 | 90.00 | — |
| Xanthan gum | — | 90.00 | 130.00 | 130.00 | 100.00 |
| Polyethylene oxide | — | 90.00 | — | — | — |
| Guar gum | — | — | — | — | 100.00 |
| Sodium bicarbonate | 100.00 | 50.00 | 39.72 | 50.00 | 50.00 |
| Citric acid | 40.00 | 20.00 | 30.28 | 20.00 | 20.00 |
| Microcrystalline cellulose | 160.00 | 60.00 | 70.00 | 70.00 | 50.00 |
| Polyvinylpyrrolidone | 70.00 | — | — | — | — |
| L-hydroxypropyl cellulose | — | 50.00 | — | — | 50.00 |
| Silicon dioxide | — | 3.00 | 3.00 | 3.00 | 3.00 |
| Magnesium stearate | 10.00 | 7.00 | 7.00 | 7.00 | 7.00 |
| Talc | 10.00 | — | — | — | — |
| Total weight | 1000.00 | 700.00 | 700.00 | 700.00 | 680.00 |

Procedure:
a) Pregabalin, swelling agent(s), gas generating agent, and other pharmaceutically acceptable excipients were sifted through a suitable sieve and thoroughly blended for a desired time;
b) Magnesium stearate was separately sifted through a suitable sieve;
c) Material of step a) was blended with the material of step b) for a suitable time; and d) The lubricated blend of step c) was compressed into tablets using appropriate tooling.

The tablets thus obtained were subjected to dissolution testing at 37° C. using United States Pharmacopoeia Type II (paddle) dissolution apparatus at 50 rpm. The dissolution medium used was 900 ml of 0.06N HCl. The results of the dissolution test are recorded in Table 1 below.

TABLE 1

| Time (hours) | Percentage of Drug Released | | | | |
|---|---|---|---|---|---|
| | Example 11 | Example 12 | Example 13 | Example 14 | Example 15 |
| 1 | 26 | 13 | 17 | 20 | 13 |
| 2 | 36 | 21 | 29 | 27 | 22 |
| 4 | 49 | 35 | 43 | 38 | 36 |
| 6 | 60 | 47 | 54 | 49 | 46 |
| 9 | 73 | 61 | 67 | 62 | 57 |
| 12 | 84 | 74 | 76 | 72 | 65 |
| 16 | 93 | 85 | 86 | 86 | 73 |
| 20 | 101 | 93 | 96 | 95 | 79 |
| 24 | 102 | 97 | 102 | 99 | 84 |

Examples 16-21

| Ingredients | Quantity (mg/tablet) | | | | | |
|---|---|---|---|---|---|---|
| | Example 16 | Example 17 | Example 18 | Example 19 | Example 20 | Example 21 |
| Pregabalin | 330.00 | 330.00 | 330.00 | 330.00 | 330.00 | 330.00 |
| Hydroxypropyl methylcellulose | 548.00 | 364.00 | — | 350.00 | — | — |
| Carbomer | — | 300.00 | 300.00 | — | 200.00 | — |
| Polyethylene oxide | — | — | 364.00 | 364.00 | — | — |
| Xanthan gum | — | — | — | — | 150.00 | 300.00 |
| Guar gum | — | — | — | — | — | 300.00 |
| Sodium alginate | — | — | — | — | 150.00 | — |
| Croscarmellose sodium | — | — | — | — | 110.00 | — |
| Sodium bicarbonate | — | 40.00 | 40.00 | 40.00 | — | — |
| Sodium carbonate | 70.00 | — | — | — | 50.00 | 60.00 |
| Citric acid | 20.00 | 10.00 | 10.00 | 10.00 | 20.00 | 20.00 |
| Microcrystalline cellulose | 120.00 | — | — | — | 78.00 | 78.00 |
| L-Hydroxypropyl cellulose | — | 50.00 | 50.00 | — | — | — |
| Silicon dioxide | 6.00 | — | — | — | 6.00 | 6.00 |
| Magnesium stearate | 6.00 | 6.00 | 6.00 | 6.00 | 6.00 | 6.00 |
| Total weight | 1100.00 | 1100.00 | 1100.00 | 1100.00 | 1100.00 | 1100.00 |

Procedure:

a) Pregabalin, swelling agent(s), gas generating agent, and other pharmaceutically acceptable excipients are sifted through a suitable sieve and thoroughly blended for a desired time;

b) Magnesium stearate is separately sifted through a suitable sieve;

c) Material of step a) is blended with the material of step b) for a suitable time; and d) The lubricated blend of step c) is compressed into tablets using appropriate tooling.

We claim:

1. A gastroretentive tablet comprising pregabalin, at least one swellable polymer, and other pharmaceutically acceptable excipients.

2. The gastroretentive tablet according to claim 1, wherein the tablet further comprises a gas generating agent.

3. The gastroretentive tablet according to claim 1, wherein the other pharmaceutically acceptable excipients are selected from diluents, binders, disintegrants, glidants, lubricants, and coloring agents.

4. The gastroretentive tablet according to claim 1, wherein the swellable polymer is selected from cellulose polymers, gums, polyethylene oxide, carbomer, superdisintegrant polymers, and combinations thereof.

5. The gastroretentive tablets according to claim 2, wherein the gas generating agent is selected from carbonates, bicarbonates, sufites, and mixtures thereof.

6. The gastroretentive tablet according to claim 5, wherein the gas generating agent additionally comprises an acid source.

7. The gastroretentive tablet according to claim 1, wherein the tablet additionally comprises a matrix forming agent.

8. The gastroretentive tablet according to claim 7, wherein the matrix forming agent is a formulated mixture of polyvinyl acetate and polyvinylpyrrolidone.

9. A process for the preparation of a gastroretentive tablet comprising pregabalin, at least one swellable polymer, and other pharmaceutically acceptable excipients selected from diluents, binders, disintegrants, glidants, lubricants, and coloring agents, wherein the process comprises the conventional methods of dry granulation, wet granulation, and direct compression.

10. The process according to claim 9, wherein the process includes using a gas generating agent.

* * * * *